(12) United States Patent
Gosh et al.

(10) Patent No.: US 6,433,204 B1
(45) Date of Patent: Aug. 13, 2002

(54) PROCESS FOR MAKING SILANOL STOPPED OLIGOMERIC MATERIALS

(75) Inventors: Nancy E. Gosh, East Greenbush; John S. Razzano, Cohoes; Slawomir Rubinsztajn, Niskayuna, all of NY (US)

(73) Assignee: General Electric Company, Pittsfield, MA (US)

( * ) Notice: Subject to any disclaimer, the term of this patent is extended or adjusted under 35 U.S.C. 154(b) by 0 days.

(21) Appl. No.: 10/055,199

(22) Filed: Jan. 23, 2002

Related U.S. Application Data

(60) Provisional application No. 60/263,911, filed on Jan. 24, 2001.

(51) Int. Cl.$^7$ .................................................. C07F 7/08
(52) U.S. Cl. ...................................................... 556/450
(58) Field of Search .......................................... 576/450

(56) References Cited

U.S. PATENT DOCUMENTS

| | | | |
|---|---|---|---|
| 3,309,390 A | | 3/1967 | Okuitanshi |
| 3,853,932 A | | 12/1974 | Razzano |
| 4,272,624 A | * | 6/1981 | Razzano .................. 556/450 X |
| 5,969,173 A | * | 10/1999 | Clarke et al. ............ 556/450 X |
| 6,316,655 B1 | * | 11/2001 | Hall et al. .................. 556/450 |

* cited by examiner

*Primary Examiner*—Paul F. Shaver
(74) *Attorney, Agent, or Firm*—Kenneth S. Wheelock

(57) ABSTRACT

A process for the production of linear silanol stopped siloxanes comprising: a) conducting a ring opening polymerization of a hexaorganocyclotrisiloxane having the formula:

$$D_3 = (R^1 R^2 SiO)_3$$

where $R^1$ and $R^2$ are independently selected from the group of one to forty carbon atom monovalent radicals, in a solvent comprising a mixture of water and a volatile polar aprotic organic solvent in the presence of catalytic amounts of a strong base; b) neutralizing the catalytic amount of the strong base with a partially neutralized salt of a polybasic acid wherein the pH ranges from about 6 to about 8; and c) washing with water.

20 Claims, No Drawings

PROCESS FOR MAKING SILANOL STOPPED OLIGOMERIC MATERIALS

CROSS-REFERENCE TO RELATED APPLICATIONS

This application claims priority to U.S. application Ser. No. 60/263,911, filed Jan. 24, 2001, which is incorporated by reference in its entirety.

FIELD OF THE INVENTION

This invention relates to a process for the production of low molecular weight silanol-stopped materials by reacting hexaorganocyclotrisiloxanes with water in the presence of catalytic amounts of a strong base. The reaction is preferably run in a water/acetone system.

BRIEF DESCRIPTION OF THE RELATED ART

Currently, silanol stopped oligomeric siloxane materials are made by two processes. The first process involves controlled hydrolysis of dichlorodimethylsilane in a water/polar solvent mixture in the presence of a neutralizing agent, such as sodium bicarbonate or ammonia. This process produces a significant amount of waste and about 30% of cyclic oligomers which have to be removed from the final product by vacuum stripping.

The second process involves ring opening polymerization of hexamethylcyclotrisiloxane in a water/ organic solvent mixture in the presence of acid-activated clay, (such as FILTROL-20) as disclosed in U.S. Pat. No. 3,853,932, or the acidic or basic ion exchange resins as described in for instance, U.S. Pat. No. 3,309,390. The process requires filtration of the catalyst and high vacuum distillation to remove cyclic oligomers formed during the ring opening polymerization.

SUMMARY OF THE INVENTION

Broadly conceived the present invention provides for a process for the production of linear silanol stopped siloxanes comprising:

a) conducting a ring opening polymerization of a hexaorganocyclotrisiloxane having the formula:

$$D_3=(R^1R^2SiO)_3$$

where $R^1$ and $R^2$ are independently selected from the group of one to forty carbon atom monovalent radicals, in a solvent comprising a mixture of water and a volatile polar, aprotic organic solvent in the presence of catalytic amounts of a strong base;

b) neutralizing the catalytic amount of the strong base with a partially neutralized salt of a polybasic acid wherein the pH ranges from about 6 to about 8; and optionally c) washing with water to remove salts, or, altenatively, stripping water and acetone from the batch and filtering the neutral salts.

DETAILED DESCRIPTION OF THE INVENTION

The present invention may be understood more readily by reference to the following detailed description of preferred embodiments of the invention and the examples included therein.

Before the present compositions of matter and methods are disclosed and described, it is to be understood that this invention is not intended to be limited to specific synthetic methods or to particular formulations, as such may, of course, vary. It is also to be understood that the terminology used herein is for the purpose of describing particular embodiments only and is not intended to be limiting.

In the following specification, reference will be made to a number of terms that shall be defined to have the following meanings:

The singular forms "a", "an" and "the" include plural referents unless the context clearly dictates otherwise.

"Optional" or "optionally" means that the subsequently described event or circumstance may or may not occur, and that the description includes instances where the event occurs and instances where it does not.

It has been discovered that a ring opening polymerization of hexamethylcyclotrisiloxane, $D_3$, in water/ volatile polar, aprotic organic solvent mixture in the presence of catalytic amounts of a strong base such as LiOH, NaOH, KOH, or a mixture thereof proceeds with a high rate to afford linear oligomeric silanol-stopped siloxanes with a high yield, typically above about 90%. The volatile polar organic solvent used with water to form the solvent of the process must be miscible with water. Non-limiting examples of such volatile polar aprotic organic solvents are low molecular weight ketones, e.g. acetone. The amount of cyclic oligomer by-product, such as octamethylcyclotetrasiloxane, D4, is very low. As used herein D3, also referred to as hexaorganocyclotrisiloxane, is defined as follows:

$$D_3=(R^1R^2SiO)_3$$

where $R^1$ and $R^2$ are independently selected from the group of one to forty carbon atom monovalent radicals where such radicals may or may not be substituted by other substituents, e.g. halogen atoms. In addition to the alkyl aralkyl and aryl groups subtended by the phrase "one to forty carbon atom monovalent radicals," this definition specifically includes, without limitation, fluoro substituted radicals such as 3,3,3-trfluoropropyl as well as perhalo-alkyl radicals and perhalo-aryl radicals.

After neutralization of the strong base with weak acids, such as carbon dioxide or acidic salts, and a subsequent water wash, the system is stable. The removal of the volatile polar aprotic organic solvent, e.g.acetone, by a simple distillation yields the desired silanol-stopped organosiloxanes with high yield. It was unexpectedly found that the process does not require filtration (because no solis are present after a water wash), and high vacuum distillation (since only small amounts of non functional cyclic siloxanes, such as octamethylcyclotetrasiloxane are formed).

With respect to neutralization, the catalyst must be neutralized to prevent condensation of the silanols during removal of solvents. It is preferable to be close to a pH 7 after neutralization of the basic catalyst preferably the pH range after neutralization is from about 6.7 to about 7.3, more preferably from about 6.5 to about 7.5 and most preferably from about 6.0 to about 8.0. This may be accomplished by measuring the base content of the reaction and precisely measuring any acid, including hydrochloric, sulfuric, acetic, etc. However, such an approach requires strict control of the concentration of acids, because if any slight excess or absence of such acids from exact stoichiometry would result in a pH which is too high or too low and cause loss of silanol during stripping. Useful deactivating agents include carbon dioxide, and acidic salts of polybasic acids. Under some conditions even carbon dioxide can produce deactivated salts which are too high in pH. As used herein polybasic acids are acids containing more than one neutralizable acid functionality per molecule, which when partially neutralized function as a buffering agent for control of pH. Therefore, most preferred are salts whose aqueous solution are close to pH 7 and which will react with the basic catalyst to produce deactivation salts which are also in the range of pH 6 to pH 8. Preferred are the monobasic salts of di- or tri-basic acids (a subset of polybasic acids). Such salts would include the partially neutralized alkali metal salts of such polybasic acids, e.g. sodium or potassium hydrogen sulfate, mono sodium or potassium oxalate and other dibasic organic acids, e.g. mono sodium or potassium dihydrogenphosphate. Most preferred is the mono sodium or potassium dihydrogenphosphate. As used herein the term alkali metal includes lithium, sodium, potassium, rubidium and cesium. By varying the molar ratio of this salt to the catalyst, the pH of the deactivated catalyst can easily be maintained near pH 7. Even when the amount of sodium dihydrogenphosphate is in excess or shortfall, the pH will remain near pH 7. The most preferred ratio is 2 moles of sodium dihydrogenphosphate per mole of basic catalyst.

The process of the present invention produces linear slioxanes in excess of 90% yield and preferably in excess of 90% yield, more preferably in excess of 95% yield and most preferably in excess of 97% yield.

The process of the present invention allows the production of linear silanol-stopped oligomers with a higher yield than known processes. The process of the present invention provides a faster rate of reaction, and the filtration step required in the prior art is eliminated by the use of a homogenous catalyst system. The process of the present invention produces less cyclic byproduct than the prior art, thereby eliminating the need for a high vacuum distillation.

EXAMPLES

The following examples are set forth to provide those of ordinary skill in the are with a complete description of how the compositions of matter and methods claimed herein are made and evaluated, and are not intended to limit the scope of what the inventors regard as their invention. Efforts have been made to insure accuracy with respect to numbers (e.g., amounts, temperature, etc.) but some errors and deviations should be accounted for. Unless indicated otherwise, parts are by weight, temperature is in ° C.

Example 1

A 1000 ml reactor equipped with condenser, mechanical stirrer and addition funnel was charged with acetone (987 g), water (50 g) and D3 (444 g, 2 mols). The reaction mixture was heated to 70° C. When temperature was stabilized, 0.042 g (0.0018 mol) of lithium hydroxide was added to start the reaction. The conversion of D3 was followed by gas chromotography. The reaction was stopped at the point when conversion of D3 was above 95%. The lithium hydroxide was neutralized by an addition of solid carbon dioxide (2 grams) into the flask. The reaction was cooled to 50° C. and was washed with 100 grams of water. The water layer was removed from the flask. Subsequently, the vacuum was slowly applied to remove the acetone and residual D3. The resulting silanol-stopped oligosiloxane (yields above 93%) was analyzed by gas chromotography.

Example 2

In an experiment, using a 500 ml flask with a condenser and a mechanical stirrer, D3 (150 grams) acetone (36 grams) and water (20 grams) were charged. The reaction mixture was heated to 61.5 to 62° C. After the temperature stabilized, 175 ppm of potassium hydroxide based on total weight was added. Samples were taken periodically to follow the reaction by gas chromatography. Samples were neutralized by the addition of carbon dioxide. The reaction continued for six hours when sodium (dihydrogen phosphate monohydrate (0.2 grams) was added to neutralize and buffer the reaction mixture. The reaction was washed three times with water. The silanol content was determined by placing a thin layer of the sample in a cup, evaporating the residual acetone, then performing an FTIR. The D3+D4 content after four hours of reaction was determined to be 5.67% and the silanol content to be 7.14%. The D3+D4 content after six hours of reaction was determined to be 5.66% and the silanol content to be about 6.95%.

An Example of the Current Art

Charge 84 g methyl trimer, 43 g of acetone, and 13 g of water into a 500 ml reaction vessel with agitator and condenser. Add 2.5 g of Filtrol 20 as a catalyst. Heat to reflux for 16 hours. G.C. analysis shows less than 5% trimer. Add 0.2 g of magnesium oxide to neutralize the Filtrol 20. Agitate and for two hours. Turn off agitation and let the batch separate for 30 minutes. Separate and discard the aqueous bottom layer. Cool until room temperature. Add 1 g of Celite 545, agitate for 10 minutes. Filter to remove all solids. Return a filtrate to a clean 500 ml flask with agitator and with vacuum capability. Add to vacuum slowly until 100 mm Hg. Then heat the batch to 120 C. Vacuum strip until D3 content and D4 content combined is less than 5% by GC. 80 g of product was isolated giving a 93% yield.

This invention has been described in detail with particular reference to preferred embodiments thereof, but it will be understood that variations and modifications can be effected within the spirit and scope of the invention.

Having described the invention, that which is claimed is:

1. A process for the production of linear silanol stopped siloxanes comprising:

a) conducting a ring opening polymerization of a hexaorganocyclotrisiloxanie having the formula:

$$D_3 = (R^1 R^2 SiO)_3$$

where $R^1$ and $R^2$ are independently selected from the group of one to forty carbon atom monovalent radicals, in a solvent comprising a mixture of water and a volatile polar, aprotic organic solvent in the presence of catalytic amounts of a strong base; and b) neutralizing the catalytic amount of the strong base with a partially neutralized salt of a polybasic acid wherein the pH ranges from about 6 to about 8.

2. The process of claim 1 further comprising the step of removing the volatile polar aprotic organic solvent.

3. The process of claim 1 where the volatile polar aprotic solvent is a low molecular weight ketone.

4. The process of claim 3 where the low molecular weight ketone is acetone.

5. The process of claim 4 where the partially neutralized salt of a polybasic acid is an alkali metal salt.

6. The process of claim 5 where the partially neutralized salt of a polybasic acid is a potassium salt.

7. The process of claim 5 where the partially neutralized salt of a polybasic acid is a sodium salt.

8. The process of claim 6 where $R^1$ is methyl.

9. The process of claim 7 where $R^1$ is methyl.

10. The process of claim 5 where $R^1$ is 3,3,3-trifluoropropyl.

11. A process for the production of linear sitanol stopped siloxanes consisting essentially of:

a) conducting a ring opening polymerization of a hexaorganocyclotrisiloxane having the formula:

$$D_3=(R^1R^2SiO)_3$$

where $R^1$ and $R^2$ are independently selected from the group of one to forty carbon atom monovalent radicals, in a solvent comprising a mixture of water and a volatile polar aprotic organic solvent in the presence of catalytic amounts of a strong base; and neutralizing the catalytic amount of the strong base with a partially neutralized salt of a polybasic acid wherein the pH ranges from about 6 to about 8. and 12. The process of claim 11 further comprising the step of removing the volatile polar aprotic organic solvent.

13. The process of claim 12 where the volatile polar aprotic solvent is a low molecular weight ketone.

14. The process of claim 13 where the low molecular weight ketone is acetone.

15. The process of claim 14 where the partially neutralized salt of a polybasic acid is an alkali metal salt.

16. The process of claim 15 where the partially neutralized salt of a polybasic acid is a potassium salt.

17. The process of claim 15 where the partially neutralized salt of a polybasic acid is a sodium salt.

18. The process of claim 16 where $R^1$ is methyl.

19. The process of claim 17 where $R^1$ is methyl.

20. The process of claim 15 where $R^1$ is 3,3,3-trifluoropropyl.

* * * * *